United States Patent [19]
Patel et al.

[11] Patent Number: 5,407,686
[45] Date of Patent: Apr. 18, 1995

[54] SUSTAINED RELEASE COMPOSITION FOR ORAL ADMINISTRATION OF ACTIVE INGREDIENT

[75] Inventors: Satischandra P. Patel, Livingston; Vinayak T. Bhalani, Morris Plains, both of N.J.

[73] Assignee: Sidmak Laboratories, Inc., East Hanover, N.J.

[21] Appl. No.: 827,604

[22] Filed: Jan. 29, 1992

Related U.S. Application Data

[63] Continuation-in-part of Ser. No. 799,344, Nov. 27, 1991, abandoned.

[51] Int. Cl.⁶ ............................................. A61K 9/22
[52] U.S. Cl. .................................. 424/468; 424/494; 424/495; 424/480
[58] Field of Search ................ 424/468, 476, 496, 475

[56] References Cited

U.S. PATENT DOCUMENTS

| | | | |
|---|---|---|---|
| 3,133,863 | 5/1964 | Tansey | 424/465 |
| 3,362,880 | 1/1968 | Jeffries | 424/470 |
| 3,492,397 | 1/1970 | Peters et al. | 424/495 |
| 3,792,157 | 2/1974 | Sheth et al. | 424/480 |
| 3,854,480 | 12/1974 | Zaffaroni | 424/424 |
| 3,948,254 | 4/1976 | Zaffaroni | 424/423 |
| 3,993,072 | 11/1976 | Zaffaroni | 424/430 |
| 4,016,880 | 4/1977 | Theeuwes et al. | 128/260 |
| 4,138,475 | 2/1979 | McAnish et al. | 424/19 |
| 4,248,856 | 2/1981 | Guley et al. | 424/21 |
| 4,248,858 | 2/1981 | Guley et al. | 424/21 |
| 4,308,251 | 12/1981 | Dunn | 424/19 |
| 4,309,405 | 1/1982 | Guley et al. | 424/21 |
| 4,309,406 | 1/1982 | Guley et al. | 424/21 |
| 4,369,172 | 1/1983 | Schor et al. | 424/19 |
| 4,459,279 | 7/1984 | Stricker et al. | 424/19 |
| 4,576,604 | 3/1986 | Guittard et al. | 604/890 |
| 4,609,374 | 9/1986 | Ayer | 604/892 |
| 4,610,870 | 9/1986 | Jain et al. | 424/19 |
| 4,615,698 | 10/1986 | Guittard et al. | 604/897 |
| 4,681,755 | 7/1987 | Colombo et al. | 424/486 |
| 4,684,516 | 8/1987 | Bhutani | 424/19 |
| 4,704,285 | 11/1987 | Alderman | 424/468 |
| 4,713,248 | 12/1987 | Kjornaes et al. | 424/468 |
| 4,721,619 | 1/1988 | Panoz et al. | 424/459 |
| 4,748,023 | 5/1988 | Tamas et al. | 424/465 |
| 4,775,535 | 10/1988 | Lowey | 424/604 |
| 4,784,858 | 11/1988 | Ventouras | 424/468 |
| 4,786,503 | 11/1988 | Edgren et al. | 424/443 |
| 4,824,678 | 4/1989 | Lindahl et al. | 424/19 |
| 4,851,228 | 7/1989 | Zentner et al. | 424/456 |
| 4,853,249 | 8/1989 | Takashima et al. | 427/3 |
| 4,891,223 | 1/1990 | Ambegaonkar et al. | 424/408 |
| 4,892,742 | 1/1990 | Shah | 424/480 |
| 4,894,223 | 1/1990 | Pigiet | 424/71 |
| 4,971,798 | 11/1990 | Coia et al. | 424/440 |
| 4,994,279 | 2/1991 | Aoki et al. | 424/496 |
| 5,002,774 | 3/1991 | Agrawala et al. | 424/468 |
| 5,093,200 | 3/1992 | Watanabe et al. | 424/476 |
| 5,133,974 | 7/1992 | Paradissis et al. | 424/475 |

FOREIGN PATENT DOCUMENTS 6203386  3/1987  Austria.
0066505 12/1982  European Pat. Off..
905000  9/1962  United Kingdom.

OTHER PUBLICATIONS

Sustained Release Medications, J. C. Johnson, Noyes Data Corporation, Park Ridge, N.J., 1980 pp. 3 and 4.
Invoice #29944, Jul. 12, 1989, to Thompson Medical Company.

Primary Examiner—Thurman K. Page
Assistant Examiner—William E. Benston
Attorney, Agent, or Firm—Sandler, Greenblum & Bernstein

[57] ABSTRACT

A sustained release tablet adapted to provide an initial immediate release of an active agent, a period of no release of the active agent, followed by a substantially constant, rate of release of the active agent. The tablet includes (a) a compressed tablet core containing an active agent, an insoluble binder and an insoluble; (b) a barrier coating formed over the tablet core, the barrier coating including a mixture of soluble and insoluble polymers and a plasticizer; (c) an active coating deposited over the barrier coating, the active coating including an active agent, a soluble polymer and a plasticizer; and (d) a film coating formed over the active coating, the film coating containing a soluble polymer and plasticizer.

36 Claims, 3 Drawing Sheets

Phenylpropanolamine HCl 75mg SR. Tablets
Release rate in water
USP Basket 100 RPM.

SUSTAINED RELEASE COMPOSITION FOR ORAL ADMINISTRATION OF ACTIVE INGREDIENT

REFERENCE TO RELATED APPLICATIONS

This application is a Continuation-In-Part application of application Ser. No. 07/799,344, filed Nov. 27, 1991, now abandoned the disclosure of which is incorporated by reference in its entirety.

BACKGROUND OF THE INVENTION

1. Field of the Invention

The present invention relates to a sustained release tablet designed or adapted to provide an immediate release of an active agent, a period of no release of an active agent, followed by a substantially constant release of the active agent.

2. Description of the Prior Art

Phenylpropanolamine hydrochloride α-(aminoethyl)benzyl alcohol hydrochloride, also known as dl-norephedrine hydrochloride, 2-amino-1-phenyl-1-propanol hydrochloride, and α-hydroxy-β-aminopropylbenzene hydrochloride), is a well-known sympathomimetic amine. Phenylpropanolamine hydrochloride is well documented as a therapeutic agent which is used as an anorexiant for control of obesity. In this capacity it has been marketed by, among others, SDA Pharmaceuticals, Inc. under the trademarks Anorexin ® and One-Span ®, and by Thompson Medical Company, Inc. under the trademark Dexatrim ®.

Phenylpropanolamine hydrochloride is also a bronchial dilator, and is accordingly used for the treatment of asthma, as well as being commonly employed as a decongestant for treatment of upper respiratory tract congestion. As an antiasthmatic, phenylpropanolamine hydrochloride has been marketed by Eaton Laboratories under the trademark Rymed ®.

U.S. Pat. No. 4,971,798 describes a slow-dissolving lozenge confection to provide slow sustained release of an antitussive, decongestant, antihistamine, or expectorant ingredient, which may be phenylpropanolamine.

U.S. Pat. No. 4,894,223 describes a novel drug delivery system for decongestants. The delivery system, which may be used to deliver phenylpropanolamine hydrochloride, is in dry particulate form, and includes a hydrophobic matrix and a coat.

It is an object of the present invention to provide a sustained release form of an active ingredient, such as Phenylpropanolamine hydrochloride, which is characterized by immediate release of the active ingredient, a period of no release of active agent, followed by release of the active ingredient at a uniform constant rate, independent of the drug concentration and/or gastrointestinal pH variation during the period of release

SUMMARY OF THE INVENTION

The object of the present invention is to provide a sustained release tablet adapted to provide an initial immediate release of an active agent, a period of no release of active agent, followed by a substantially constant, zero-order rate of release of the active agent.

The tablet of the present invention comprises:
(a) a compressed tablet core comprising an active agent, an insoluble binder and an insoluble filler;
(b) a barrier coating formed over the tablet core, the barrier coating comprising a mixture of soluble and insoluble polymers, and a plasticizer;
(c) an active coating formed over the barrier coating, the active coating comprising the active agent, a soluble polymer and a plasticizer; and
(d) a film coating formed over the active coating, the film coating comprising a soluble polymer and a plasticizer.

The active agent is contained in the active coating in an amount of from about 1 to about 35% by weight of the total dosage weight of the active agent in the sustained release tablet. Preferably, the active agent is phenylpropanolamine hydrochloride, which may be present in the active coating in an amount of from about 15 to about 33% by weight, of the total dosage weight of the phenylpropanolamine hydrochloride in the tablet. Other active agents may be employed, however, including, but not limited to, to adrenergic agents, anticholinergic agents; antispasmodic agents; curariform agents; tranquilizers; muscle relaxants; antihistamines; hypotensive agents; cardioactive agents; angiotensin converting enzyme inhibitors; bronchodilators; steroids; antibacterial agents; antimalarials; antibiotics; sedatives; and analgesics.

The sustained release tablet of the present invention has a typical release profile of the active agent in the tablet, as measured in the in-vitro dissolution method utilizing U.S.P. XXII, basket method at 100 RPM in water at 37° C., as follows:

| | |
|---|---|
| 1 hour | 15–33% |
| 2 hours | No release |
| 3–4 hours | 4–6%/hour |
| 5–6 hours | 4–6%/hour |
| 7–8 hours | 4–6%/hour |
| 9–10 hours | 4–6%/hour |
| 11–12 hours | 3–5%/hour |
| 13–14 hours | 3–5%/hour |

The sustained release tablet according to the present invention comprises:
(a) a compressed tablet core comprising phenylpropanolamine hydrochloride, ethyl cellulose and calcium sulfate;
(b) a barrier coating formed over the tablet core, the barrier coating comprising a mixture of hydroxypropyl methyl cellulose, ethyl cellulose and glyceryl triacetate, wherein the hydroxypropyl methyl cellulose and the ethyl cellulose are utilized in a ratio by weight of about 1:3;
(c) an active coating formed over the barrier coating, the active coating comprising phenylpropanolamine hydrochloride, hydroxypropyl methyl cellulose and glyceryl triacetate, wherein the amount of phenylpropanolamine hydrochloride in the active coating is from about 15 to about 33% by weight of the total dosage weight of the phenylpropanolamine hydrochloride in the tablet; and
(d) a film coating formed over the active coating, the film coating comprising hydroxypropyl methyl cellulose and glyceryl triacetate.

The present invention also contemplates a method of preparing the novel sustained release tablet of the invention. According to a preferred method, a sustained release tablet adapted to provide an initial immediate release of an active agent, a period of no release of active agent, followed by a substantially constant, zero-order rate of release of the active agent is provided by a method which comprises:
 (a) forming a compressed tablet core comprising an active agent, an insoluble binder and a filler;
 (b) coating the tablet core with a barrier coating comprising a mixture of soluble and insoluble polymers, and a plasticizer;
 (c) coating the barrier coating with an active coating comprising an active agent, a soluble polymer and a plasticizer; and
 (d) coating the active coating with a film coating comprising a soluble polymer and a plasticizer.

The present invention also contemplates a method of inducing appetite suppression in a human, the method which comprises administering to the human a sustained release tablet adapted to provide an initial immediate release of phenylpropanolamine hydrochloride, a period of no release of active ingredient, followed by a substantially constant, zero-order rate of release of phenylpropanolamine hydrochloride, the tablet comprising:
 (a) a compressed tablet core comprising phenylpropanolamine hydrochloride, ethyl cellulose and calcium sulfate;
 (b) a barrier coating formed over the tablet core, the barrier coating comprising a mixture of hydroxypropyl methyl cellulose, ethyl cellulose and glyceryl triacetate, wherein the hydroxypropyl methyl cellulose and the ethyl cellulose are utilized in a ratio by weight of about 1:3;
 (c) an active coating formed over the barrier coating, the active coating comprising phenylpropanolamine hydrochloride, hydroxypropyl methyl cellulose and glyceryl triacetate, wherein the amount of phenylpropanolamine hydrochloride in the active coating is from about 15 to about 33% by weight of the total dosage weight of the phenylpropanolamine hydrochloride in the tablet; and
 (d) a film coating formed over the active coating, the film coating comprising hydroxypropyl methyl cellulose and glyceryl triacetate.

DETAILED DESCRIPTION OF THE INVENTION

In accordance with the present invention, a sustained release tablet is adapted to provide an initial immediate release of an active agent, a period of no release of active agent, followed by a substantially constant, zero-order rate of release of the active agent is provided. The tablet comprises:
 (a) a compressed tablet core comprising of an active agent, an insoluble binder and an insoluble filler;
 (b) a barrier coating formed over the tablet core, the barrier coating comprising of a mixture of soluble and insoluble polymers and a plasticizer;
 (c) an active coating formed over the barrier coating, the active coating comprising the active agent, a soluble polymer and a plasticizer; and
 (d) a film coating formed over the active coating, the film coating comprising a soluble polymer and a plasticizer.

Generally, sustained release dosage forms release their drug contents gradually after the drug makes contact with alimentary fluids, dampening the peaks and valleys observed with immediate release dosage forms. The drug concentration is also maintained in the body for longer periods of time, reducing the frequency of dosage. However, most sustained release products do not produce uniform blood concentration levels over a prolonged period of time. Initially, the rate of drug release increases rapidly, followed by an exponentially declining rate of release. This type of drug release is categorized as a first-order release mechanism.

In contrast, the sustained release tablets of the present invention provide an initial immediate release of active agent and a period of no release of active agent, followed by a substantially constant rate of release. The sustained release tablet according to the present invention provides initial immediate release of active agent, which is just sufficient to build initial concentration of active agent in the blood. In the period of no release, the blood concentration of active agent slowly declines to a desired level at which constant release period of the dosage form kicks in, providing substantially constant rate of release for a desired time period.

A wide variety of medicaments which are orally administered in tablet form can be used in the sustained release tablet prepared according to this invention. These include, for example, adrenergic agents, such as ephedrine, desoxyephedrine, phenylephrine, epinephrine and the like; cholinergic agents, such as, physostigmine, neostigmine and the like; antispasmodic agents, such as atropine, methantheline, papaverine and the like; curariform agents, such as, chlorisondamine and the like; tranquilizers and muscle relaxants, such as fluphenazine, chlorpromazine, trifluoperazine, mephenesin, meprobamate and the like; antihistamines, such as diphenhydramine, dimenhydrinate, tripelennamine, perphenazine, chlorprophenazine, chlorprophenpyridamine and the like; hypotensive agents, such as rauwolfia, reserpine and the like; cardioactive agents, bendroflumethiazide, chlorothiazide, aminotrate, propranolol, nadolol, procainamide and the like, angiotensin converting enzyme inhibitors, such as, captopril, enalapril, and the like; bronchodilators, such as, phenylpropanolamine hydrochloride, theophylline, and the like; steroids, such as, testosterone, prednisolone, and the like; antibacterial agents, e.g., sulfonamides, such as sulfadiazine, sulfamerazine, sulfamethazine, sulfisoxazole and the like, antimalarials, such as, chloroquine and the like; antibiotics such as the tetracyclines, nystatin, streptomycin, cephradine and other cephalosporins, penicillin, semi-synthetic penicillins, griseofulvin and the like; sedatives, such as chloral hydrate, phenobarbital and other barbiturates, glutethimide, antitubercular agents, such as isoniazid and the like; and analgesics, such as aspirin, acetaminophen, propoxyphene, meperidine and the like.

These substances are frequently employed either as the free compound or in a salt form, for example, acid addition salts or basic salts such as alkali metal salts. Other therapeutic agents having the same or different physiological activity can also be employed in pharmaceutical preparations within the scope of the present invention.

A preferred active agent is phenylpropanolamine hydrochloride, a known decongestant and appetite suppressant. Any commercially available forms of phenylpropanolamine hydrochloride may be used in accordance with the present invention.

In the present invention, the compressed tablet core contains active agent, insoluble binder and an insoluble filler and lubricant. The active ingredient in the core may contain any therapeutic agent, including any of those described above, however, preferably contains phenylpropanolamine hydrochloride. The active agent constitutes about 30 to 80% by weight of the core, preferably about 60% by weight of the core ingredient. The insoluble binder could be ethyl cellulose, cellulose acetate, cellulose tributarate, and is most preferably ethyl cellulose having a viscosity of 5 to 50 cps. The concentration of the insoluble binder varies between 2 to 20% by weight, preferably about 15% by weight. The insoluble filler could be any insoluble excipient, organic or inorganic in nature, preferably calcium sulfate. The concentration of the insoluble filler averages between 10 to 30% by weight, preferably about 20% by weight. The core contains a suitable lubricant, preferably stearic acid and magnesium stearate.

In the barrier coating, soluble and insoluble polymers, together with plasticizers, are utilized. The soluble polymer comprises hydroxpropylmethylcellulose, hydroxypropylcellulose, hydroxyethylcellulose, methycellulose and carboxymethylcellulose. The preferred soluble polymer for the present invention is hydroxypropylmethylcellulose, and preferably the hydroxypropylmethylcellulose has a viscosity of 3 to 100 cps, with the most preferred viscosity being 15 cps. The insoluble polymer of the present invention comprises ethyl cellulose, cellulose acetate, cellulose tributarate; the preferred insoluble polymer of this invention is ethyl cellulose. The viscosity range of ethyl cellulose is the range of 5 to 50 cps, with the preferred viscosity being 10 cps. The ratio of soluble polymer to insoluble polymer ranges from 1:1 to 1:10, preferably 1:3. The plasticizer added to the barrier coating consists of glyceryl triacetate, triethyl citrate, diethyl phthalate, polyethylene glycol, glycerin, castor oil and the like. The preferred plasticizer of the present invention is glyceryl triacetate. The concentration of the plasticizer in the barrier coating is about 5 to 20% by weight, preferably about 10% by weight, based on the total weight of the soluble and insoluble weight of the polymer in the barrier coating.

The active coating is formed over the barrier coating, and comprises phenylpropanolamine hydrochloride, hydroxypropylmethylcellulose, having a viscosity of 15 cps, glyceryl triacetate, and polyvinyl pyrrollidone. The amount of phenylpropanolamine hydrochloride in the active coating is in the range of 15 to 33% on the basis of the total weight of phenylpropanolamine hydrochloride in the tablet. The outer coating comprises hydroxypropylmethylcellulose, having a viscosity of 15 cps, and glyceryl triacetate.

The amounts of the above-indicated tablet components may be varied in accordance with principles known in the art to provide sustained release tablets having different release properties. For example, the ratio of soluble polymer to insoluble polymer in the barrier coating may be varied. The blend of polymers and plasticizers in the barrier coating provides a mesh-like porous structure around the tablet core which enables dissolution and diffusion of the active agent at a substantially constant, zero-order rate of release. Similarly, the thickness of each of the barrier, active, and film coatings may be manipulated so as to affect the initial release of active agent from the active layer as well as the subsequent sustained release of active agent from the tablet core. For example, increasing the thickness of the barrier coating will lower the rate of release of the active agent from the tablet core. Selection of a suitable thickness, based on the particular active agent and desired dosage levels, may be readily carried out by those of ordinary skill in the art.

Thus, in a preferred aspect of the present invention a sustained release tablet adapted to provide an initial immediate release of phenylpropanolamine hydrochloride, a period of no release of phenylpropanolamine hydrochloride, followed by a substantially constant, rate of release of phenylpropanolamine hydrochloride is provided by a tablet which comprises:

(a) a compressed tablet core comprising phenylpropanolamine hydrochloride, ethyl cellulose and calcium sulfate;

(b) a barrier coating formed over the tablet core, the barrier coating comprising a mixture of hydroxypropyl methyl cellulose, ethyl cellulose and glyceryl triacetate, wherein the hydroxypropyl methyl cellulose and the ethyl cellulose are utilized in a ratio by weight of about 1:3;

(c) an active coating formed over the barrier coating, the active coating comprising phenylpropanolamine hydrochloride, hydroxypropyl methyl cellulose and glyceryl triacetate, wherein the amount of phenylpropanolamine hydrochloride in the active coating is from about 15 to about 33% by weight of the total dosage weight of the phenylpropanolamine hydrochloride in the sustained release tablet; and (d) a film coating formed over the active coating, the film coating comprising hydroxypropyl methyl cellulose and glyceryl triacetate.

The tablets of the invention may also include those additional ingredients well-known in the pharmaceutical art, such as colorants, film formers, preservatives, excipients, tableting lubricants, anti-adherents, and binders. Exemplary anti-adherents include silicon dioxide and water. A preferred tableting lubricant used in the formulations of the invention comprises a mixture of stearic acid and magnesium stearate.

The present invention also contemplates a method of preparing a sustained release tablet adapted to provide an initial immediate release of an active agent, a period of no release of active agent, followed by a substantially constant rate of release of the active agent, the method which comprises:

(a) forming a compressed tablet core comprising an active agent, an insoluble polymer and a filler;

(b) coating the tablet core with a barrier coating comprising a mixture of soluble and insoluble polymers, and a plasticizer;

(c) coating the barrier coating with an active coating comprising an active agent, a soluble polymer and a plasticizer; and (d) coating the active coating with a film coating comprising a soluble polymer and a plasticizer.

The tablet core is preferably formed according to techniques known in the art. These involve granulating a mixture comprising active agent and filler with a solution comprising insoluble polymer and organic solvent to form a granulated blend; drying the granulated blend to form a solid; and compressing this solid to form the core. A preferred organic solvent for the core granulation is isopropanol. Drying temperatures in the range of 30° to 40° C. are preferred, but any suitable range may be employed. Drying may be carried out in the blender utilized during granulation, in a fluid bed drier, or in a drying area/Lydon oven.

The barrier coating is preferably formed by preparing a barrier coating solution comprising a mixture of soluble and insoluble polymers, plasticizer and organic solvent; and spray coating the barrier coating solution over the tablet core. The organic solvent used to prepare the barrier coating is preferably a solution comprising methylene chloride and methanol, employed in equal-volume amounts.

Similarly, the active coating is preferably formed by a preparing an active coating solution comprising an active agent, a soluble polymer, a plasticizer and an organic solvent; and spray coating the active coating solution over the barrier coating. An equal-volume solution of methylene chloride and methanol is the preferred organic solvent used in forming the active coating.

The film coating may be formed by any conventional technique known in the art, but preferably is formed by preparing a film coating solution comprising a soluble polymer, a plasticizer, and an organic solvent, along with coloring agents, opacifiers such as titanium dioxide and talc, perfumes, and the like; and spray coating the film coating solution over the active coating. Again, an equal volume solution of methylene chloride and methanol is the preferred organic solvent.

Other coating techniques known in the art for forming tablet coatings may be employed instead of the preferred spray coating method. Exemplary alternative coating techniques include conventional pan coating and centrifugal liquid-bed coating methods. Upon oral administration, the film coating and active coating are dissolved by the action of gastrointestinal fluids to provide an immediate release of the active agent contained in the active coating. The period of up to no release is a period of no release of active agent produced due to the special nature of the core and coating composition. Subsequently, the barrier coating permits the active agent to diffuse out of the tablet core at a substantially constant, zero-order rate of release.

As indicated above, the sustained release tablets of the invention are advantageously usable with a wide variety of active agents. In a preferred embodiment, the active agent is phenylpropanolamine hydrochloride, an active agent which is desirably administered so as to achieve an immediate effect, a period of no release of active agent, followed by a constant rate of release over a prolonged period of time.

Thus, the present invention contemplates a method of inducing appetite suppression in a human, the method which comprises administering to the human a sustained release tablet adapted to provide an initial immediate release of phenylpropanolamine hydrochloride, a period of no release of phenylpropanolamine hydrochloride, followed by a substantially constant, zero-order rate of release of phenylpropanolamine hydrochloride, the tablet which comprises:

(a) a compressed tablet core comprising phenylpropanolamine hydrochloride, ethyl cellulose and calcium sulfate;

(b) a barrier coating formed over the tablet core, the barrier coating comprising a mixture of hydroxypropyl methyl cellulose, ethyl cellulose and glyceryl triacetate, wherein the hydroxypropyl methyl cellulose and the ethyl cellulose are utilized in a ratio by weight of about 1:3;

(c) an active coating formed over the barrier coating, the active coating comprising phenylpropanolamine hydrochloride, hydroxypropyl methyl cellulose and glyceryl triacetate, wherein the amount of phenylpropanolamine hydrochloride in the active coating is from about 15 to about 33% by weight of the total dosage weight of the phenylpropanolamine hydrochloride in the tablet; and (d) a film coating formed over the active coating, the film coating comprising hydroxypropyl methyl cellulose and glyceryl triacetate.

It has been found that when phenylpropanolamine hydrochloride is administered according to the invention, appetite suppression occurs immediately and is sustained for 12 to 24 hours.

EXAMPLES

The following examples are given to illustrate the invention, but are not deemed to be limiting thereon.

The following examples illustrate the preparation of sustained release tablets in accordance with the present invention.

Example 1

Formulation of Sustained Release Tablet

The below listed ingredients were utilized to prepare a phenylpropanolamine hydrochloride 75 mg sustained release tablet:

| INGREDIENTS | Mg. Tablet | % BY WEIGHT |
| --- | --- | --- |
| Core | | |
| Phenylpropanolamine HCl U.S.P. | 60.000 | 44.45 |
| Calcium Sulfate Anhydrous N.F. | 19.000 | 14.07 |
| Ethyl Cellulose N.F. | 15.500 | 10.74 |
| *Isopropyl Alcohol U.S.P. | (0.012 cc) | 0.01 |
| Stearic Acid N.F. | 6.000 | 4.45 |
| Magnesium Stearate N.F. | 0.500 | 0.37 |
| Barrier Coating | | |
| Hydroxypropyl Methyl Cellulose U.S.P. | 1.292 | 0.96 |
| Ethyl Cellulose N.F. | 3.818 | 2.83 |
| Triacetin U.S.P. (0.0005 cc) | 0.510 | 0.38 |
| *Methylene Chloride N.F. | (0.0586 cc) | 0.04 |
| *Methanol N.F. | (0.0586 cc) | 0.04 |
| Active Coating | | |
| Phenylpropanolamine HCl U.S.P. | 20.000 | 14.82 |
| Povidone U.S.P. | 1.244 | 0.92 |
| Hydroxypropyl Methyl Cellulose U.S.P. | 0.374 | 0.28 |
| Triacetin U.S.P. (0.0025 cc) | 2.865 | 2.13 |
| *Isopropyl Alcohol U.S.P. | (0.0248 cc) | 0.02 |
| *Purified Water U.S.P. | (0.0124 cc) | 0.01 |
| Film coating | | |
| *Methylene Chloride N.F. | (0.0572 cc) | 0.04 |
| *Methanol N.F. | (0.0352 cc) | 0.03 |
| Triacetin U.S.P. (0.0004 cc) | 0.464 | 0.35 |
| Hydroxypropyl Methyl Cellulose U.S.P. | 3.200 | 2.37 |
| D & C Yellow #10 A1 Lake | 0.160 | 0.12 |
| FD & C Yellow #6 A1 Lake | 0.064 | 0.05 |
| Titanium Dioxide U.S.P. | 0.960 | 0.71 |

-continued

| INGREDIENTS | Mg. Tablet | % BY WEIGHT |
|---|---|---|
| Total Solids: | 135 mg. | 100% |

*Does not appear in finished product.

Example 2

Formulation of Sustained Release Tablet

The below listed ingredients were utilized to prepare a phenylpropanolamine hydrochloride 75 mg sustained release tablet:

| INGREDIENTS | % BY WEIGHT |
|---|---|
| CORE: | |
| Phenylpropanolamine HCl USP | 44.45 |
| Calcium Sulfate Anhydrous NF | 14.07 |
| Ethyl Cellulose NF | 10.74 |
| *Isopropyl Alcohol USP | 0.01 |
| Stearic Acid NF | 4.45 |
| Magnesium Stearate NF | 0.37 |
| BARRIER COATING | |
| Hydroxypropyl Methyl Cellulose USP | 1.14 |
| Ethyl Cellulose NF | 2.65 |
| Triacetin USP | 0.38 |
| *Methylene Chloride NF | 0.04 |
| *Methanol NF | 0.04 |
| ACTIVE COATING | |
| Phenylpropanolamine HCl USP | 14.82 |
| Povidone USP | 0.92 |
| Hydroxypropyl Methyl Cellulose USP | 0.28 |
| Triacetin USP | 2.13 |
| *Isopropyl Alcohol USP | 0.02 |
| *Purified Water USP | 0.01 |
| FILM COATING | |
| *Methylene Chloride NF | 0.04 |
| *Methanol NF | 0.03 |
| Triacetin USP | 0.35 |
| Hydroxypropyl Methyl Cellulose USP | 2.37 |
| D & C Yellow #10 A1 Lake | 0.12 |
| FD & C Yellow #6 A1 Lake | 0.05 |
| Titanium Dioxide U.S.P. | 0.71 |
| TOTAL SOLIDS: | 100% |

*Does not appear in finished product.

Example 3

Preparation of Sustained Release Tablet

The ingredients of Examples 1 and 2 were formed into sustained release tablets by the following steps.

1. Tablet Core: A granulation premix is prepared by blending the filler, active agent and about 92% of the insoluble binder for about ten minutes after screening each ingredient through a #18 mesh screen. A granulation solution is prepared by mixing the remainder of the insoluble binder with the organic solvent, while warming the solution to about 40° to 50° C. The premix and granulation solution are granulated, whereupon the resulting granulated blend is dried at 30° to 40° C., milled, screened through a #18 mesh screen, and redried at 40° to 50° C. until the loss on drying is less than 2%. The lubricant is blended with the resulting solid for about 5 minutes. Finally, the solid is compressed to form the tablet core.

2. Barrier coating: A barrier coating solution is prepared by mixing the soluble polymer, insoluble polymer, plasticizer and organic solvent. The tablet core from Step 1 is spray coated with the barrier coating solution to provide a barrier coating of about 5% by weight per tablet on a final weight basis.

3. Active coating: An active coating solution is prepared by mixing the active agent, soluble polymer, plasticizer, povidone, organic solvent and water. The barrier coated tablet core from Step 2 is spray coated with the active coating solution to provide an active coating having a desired weight gain to provide the desired weight percent of active agent in the active coating, which is preferably for phenylpropanolamine hydrochloride in the range of 15 to 33% on the basis of the total weight of phenylpropanolamine hydrochloride in the tablet.

4. Film coating: A film coating solution is prepared by blending the soluble polymer, plasticizer, organic solvent, titanium dioxide and colorant. The barrier/active coated tablet core from Step 3 is spray coated with the film coating solution to form a film coating having a desired thickness film coating thickness.

Example 4

Figure 1:
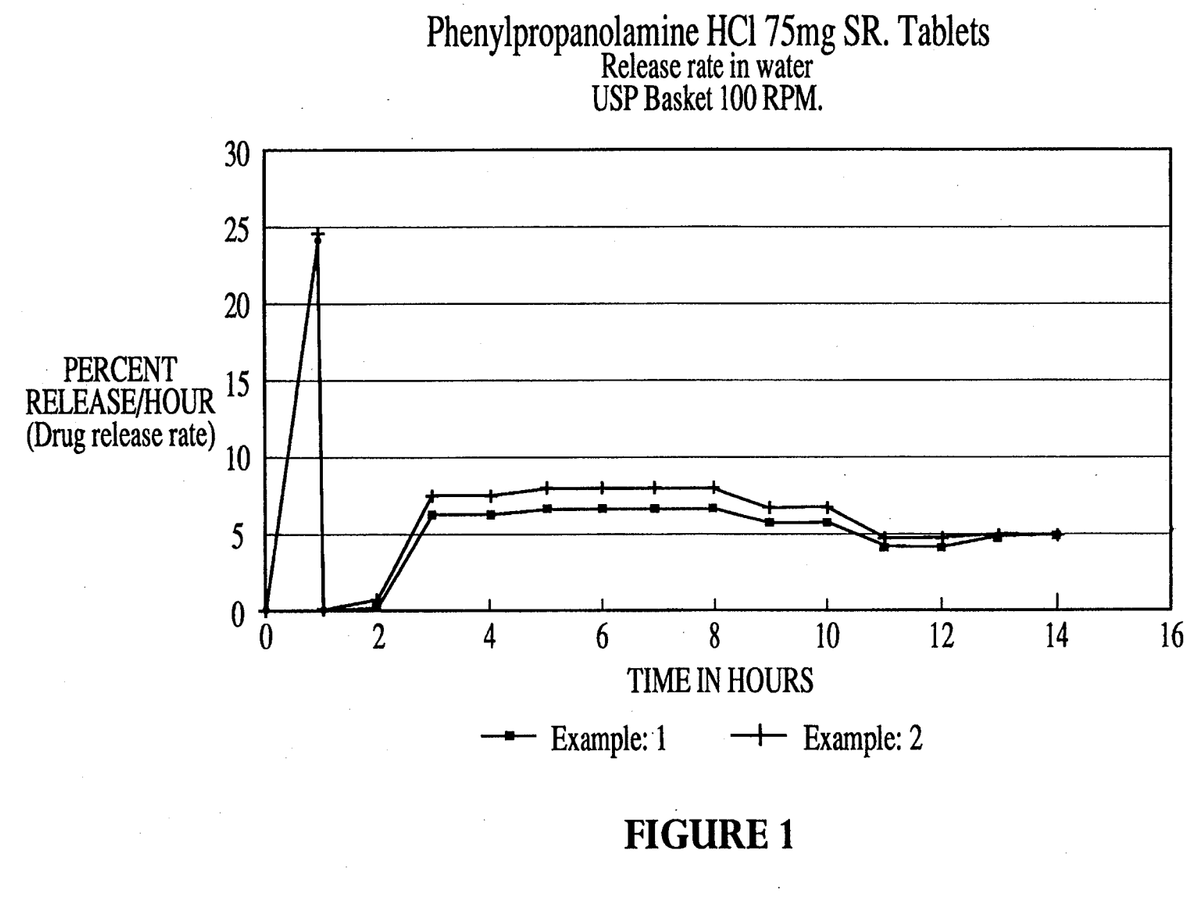
FIG. 1 shows the release rate profile of Phenylpropanolamine Hydrochloride Sustained Release Tablet for Examples 1 and 2 according to the present invention showing immediate release, a period of no release, followed by constant release period.

The thus formed tablets were tested by the in vitro dissolution method utilizing the U.S.P XXII basket method at 100 RPM in water at 37° C. The results of this test are illustrated in FIG. 1 wherein the release rate using the Example 1 formulation are depicted with the dotted line ("."), and the release rate using the Example 2 formulation are depicted with the crossed line ("+").

Figure 2:
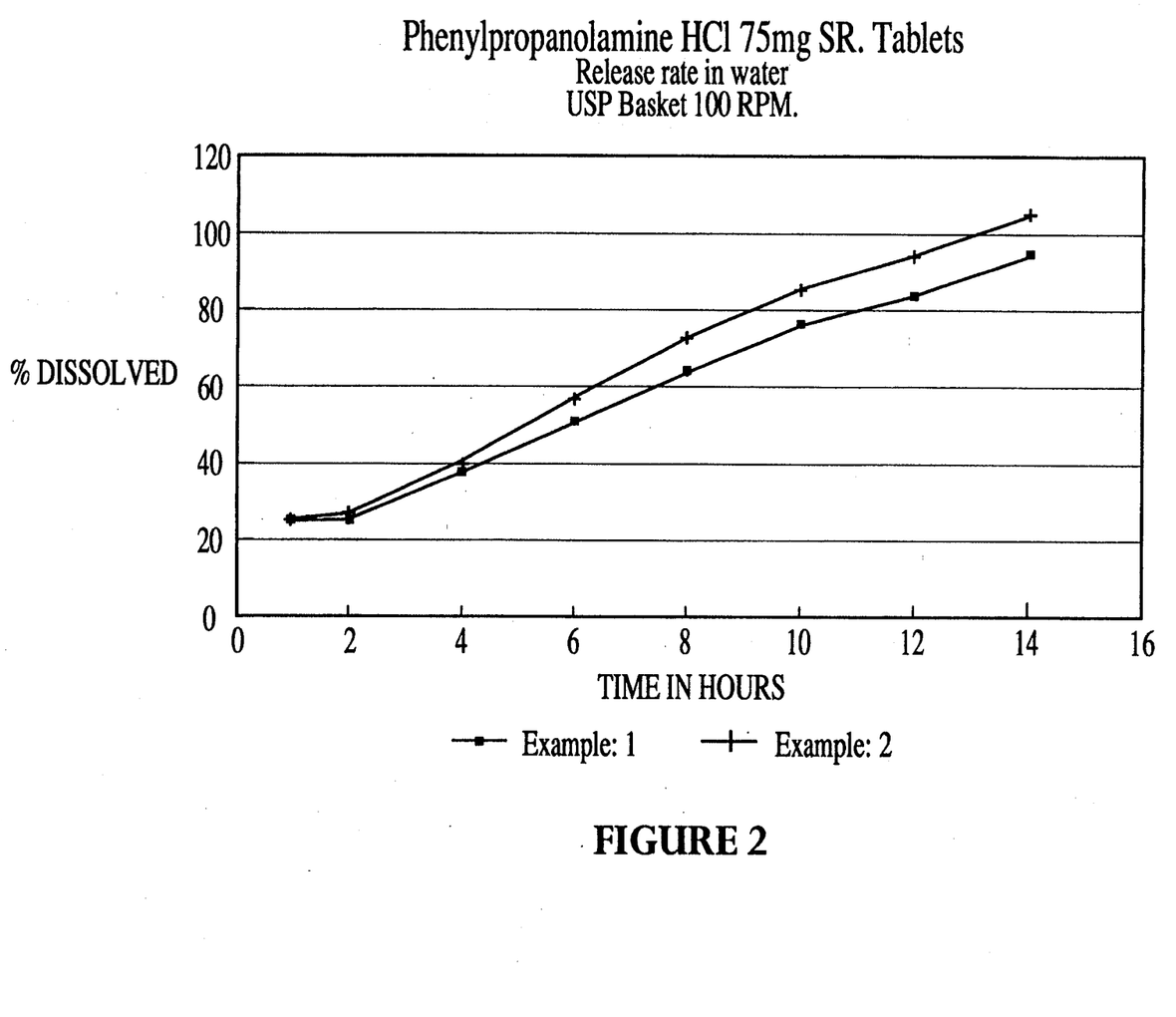
FIG. 2 shows the percent dissolved vs. time of Phenylpropanolamine Hydrochloride Sustained Release Tablet for Examples 1 and 2 according to the present invention showing immediate release, a period of no release, followed by constant release period.

Further, the results for Examples 1 and 2 are illustrated in FIG. 2 where the % dissolved is plotted against time. The results of FIG. 2 are tabulated in Table 1, which presents the in vitro percent release of each of the 75 mg sustained release tablets of Example 1 and Example 2.

TABLE 1

Phenylpropanolamine Hydrochloride Sustained Release Tablets
In-Vitro release rate in water USP Basket 100 RPM

| | % RELEASE | | | | | | | |
|---|---|---|---|---|---|---|---|---|
| EX-AMPLE | 1 HR | 2 HR | 4 HR | 6 HR | 8 HR | 10 HR | 12 HR | 14 HR |
| Example: 1 | 24 | 24 | 37 | 50 | 63 | 75 | 83 | 93 |
| Example: 2 | 24.5 | 24.9 | 39.9 | 55.9 | 71.7 | 84.7 | 94.3 | 104.1 |

FIG. 2 and Table 1 illustrate that the sustained release tablet of the present invention exhibits an initial immediate release of active agent upon administration, a period of no release of active agent, followed by a substantially constant, zero-order rate of release of the active agent.

Release Rate Studies

In-Vitro Release Profile:

The in-vitro release profile of sustained release tablet was determined using U.S.P. XXII method, using rotating basket at 100 rpm in 1000 cc of water at 37° C. The amount of drug released per hour was determined by HPLC. The typical release rate profile is shown in Table I and in FIG. 1 for Examples 1 and 2. As discussed above, the sustained release tablet of the present invention has a typical release profile of the active agent in the tablet, as measured in the in-vitro dissolution method utilizing U.S.P. XXII, basket method at 100 RPM in water at 37° C., as follows:

| 1 hour | 15–33% |
|---|---|
| 2 hours | No release |
| 3–4 hours | 4–6%/hour |

-continued

| | |
|---|---|
| 5-6 hours | 4-6%/hour |
| 7-8 hours | 4-6%/hour |
| 9-10 hours | 4-6%/hour |
| 11-12 hours | 3-5%/hour |
| 13-14 hours | 3-5%/hour |

Figure 3:
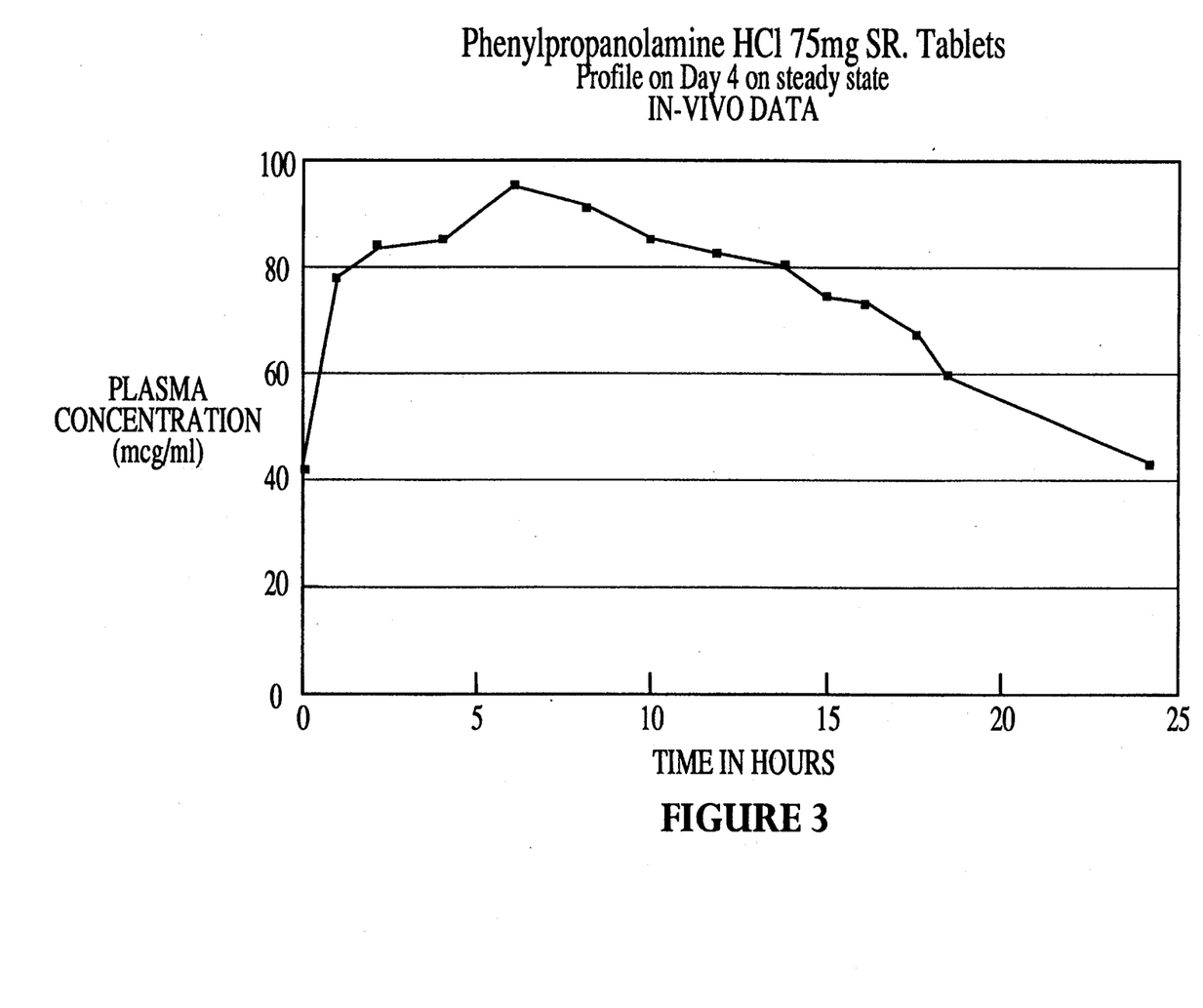
FIG. 3 shows in vivo data of the plasma concentration of a Phenylpropanolamine Hydrochloride Sustained Release Tablet of phenylpropanolamine hydrochloride on day 4 of treatment.

In-Vivo Release Profile:

In-vivo blood level studies of sustained release tablets were performed on six normal subjects in multiple dose fasting conditions. The typical blood level data is shown in FIG. 3 for the sustained release tablet of the present invention. In particular, the typical in-vivo plasma level profile produces constant plasma level in the rate of 50 to 90 mcg./ml. for up to 16-20 hours.

The present invention has of necessity been discussed herein by reference to certain specific methods, materials, and configurations. It is to be understood that the discussion of these specific methods, materials and configurations in no way constitutes any limitation on the scope of the present invention, which extends to any and all alternative methods, materials and configurations suitable for accomplishing the ends of the present invention.

What is claimed is:

1. A sustained release tablet, comprising:
   a plurality of layers; and
   said plurality of layers being constructed and arranged to provide an initial immediate release of an active agent, a period of no release of active agent, followed by a substantially constant rate of release of said active agent.

2. The sustained release tablet of claim 1, wherein said active agent is phenylpropanolamine hydrochloride.

3. The sustained release tablet of claim 2, wherein said plurality of layers comprise:
   (a) a compressed tablet core comprising an active agent, an insoluble binder and a filler;
   (b) a barrier coating formed over said compressed tablet core, said barrier coating comprising a mixture of soluble and insoluble polymers and a plasticizer;
   (c) an active coating formed over said barrier coating, said active coating comprising an active agent, a soluble polymer and a plasticizer; and
   (d) a film coating formed over said active coating, said film coating comprising a soluble polymer and a plasticizer.

4. The sustained release tablet of claim 3, wherein said active coating contains said phenylpropanolamine hydrochloride in an amount of from about 15 to about 33% by weight of the total dosage weight of said phenylpropanolamine hydrochloride in the tablet.

5. The sustained release tablet of claim 3, wherein the typical release profile of the active agent in the tablet is the following (in-vitro dissolution method utilizing U.S.P. XXII, basket method at 100 RPM in water at 37° C.):

| | |
|---|---|
| 1 hour | 15-33% |
| 2 hours | No release |
| 3-4 hours | 4-6%/hour |
| 5-6 hours | 4-6%/hour |
| 7-8 hours | 4-6%/hour |
| 9-10 hours | 4-6%/hour |
| 11-12 hours | 3-5%/hour |
| 13-14 hours | 3-5%/hour |

6. The sustained release tablet of claim 3, wherein the typical in-vivo plasma level profile produces constant plasma level in the rate of 50 to 90 mcg./ml. for up to 16-20 hours.

7. The sustained release tablet of claim 1, wherein said plurality of layers comprise a core, a barrier coating, an active coating and a film coating.

8. The sustained release tablet of claim 7, wherein said active agent is phenylpropanolamine hydrochloride.

9. The sustained release tablet of claim 8, wherein the typical release profile of the active agent in the tablet is the following (in-vitro dissolution method utilizing U.S.P. XXII, basket method at 100 RPM in water at 37° C.):

| | |
|---|---|
| 1 hour | 15-33% |
| 2 hours | No release |
| 3-4 hours | 4-6%/hour |
| 5-6 hours | 4-6%/hour |
| 7-8 hours | 4-6%/hour |
| 9-10 hours | 4-6%/hour |
| 11-12 hours | 3-5%/hour |
| 13-14 hours | 3-5%/hour |

10. The sustained release tablet of claim 8, wherein the typical in-vivo plasma level profile produces constant plasma level in the rate of 50 to 90 mcg./ml. for up to 16-20 hours.

11. The sustained release tablet of claim 8, wherein said active coating contains said phenylpropanolamine hydrochloride in an amount of from about 15 to about 33% by weight of the total dosage weight of said phenylpropanolamine hydrochloride in the tablet.

12. A sustained release tablet constructed and arranged to provide an initial immediate release of an active agent, a period of no release of active agent, followed by a substantially constant, zero-order rate of release of said active agent, said tablet comprising:
   (a) a compressed tablet core comprising an active agent, an insoluble polymer and a filler;
   (b) a barrier coating formed over said compressed tablet core, said barrier coating comprising a mixture of soluble and insoluble polymers and a plasticizer;
   (c) an active coating formed over said barrier coating, said active coating comprising an active agent, a soluble polymer and a plasticizer; and
   (d) a film coating formed over said active coating, said film coating comprising a soluble polymer and plasticizer.

13. The sustained release tablet of claim 12, wherein said insoluble polymer in said tablet core and said barrier coating comprises ethyl cellulose.

14. The sustained release tablet of claim 12, wherein said soluble polymer in said barrier coating is selected from the group consisting of hydroxypropyl methylcellulose, hydroxypropyl cellulose, methylcellulose, carboxymethyl cellulose, and mixtures thereof.

15. The sustained release tablet of claim 12, wherein said soluble polymer in said barrier coating, said active coating, and said film coating comprises hydroxypropyl methyl cellulose.

16. The sustained release tablet of claim 12, wherein said filler is an organic or inorganic insoluble material.

17. The sustained release tablet of claim 12, wherein said filler comprises calcium sulfate.

18. The sustained release tablet of claim 12, wherein said barrier coating comprises a mixture of hydroxypropyl methyl cellulose, ethyl cellulose, and a plasticizer, and further wherein the ratio by weight of said hydroxypropyl methyl cellulose to said ethyl cellulose is from about 1:1 to about 1:10.

19. The sustained release tablet of claim 18, wherein the ratio by weight of said hydroxypropyl methyl cellulose to said ethyl cellulose is about 1:3.

20. The sustained release tablet of claim 12, wherein said active coating contains said active agent in an amount of from about 1 to about 35% by weight of the total dosage weight of said active agent in the tablet.

21. The sustained release tablet of claim 20, wherein said active coating contains said active agent in an amount of from about 15 to about 33% by weight of the total dosage weight of said active agent in the tablet.

22. The sustained release tablet of claim 20, wherein said active agent in said tablet core and said active coating comprises phenylpropanolamine hydrochloride.

23. The sustained release tablet of claim 22, wherein said active coating contains said phenylpropanolamine hydrochloride in an amount of from about 15 to about 33% by weight of the total dosage weight of said phenylpropanolamine hydrochloride in the tablet.

24. The sustained release tablet of claim 12, wherein said active agent is selected from the group consisting of adrenergic agents; cholinergic agents; antispasmodic agents; curariform agents; tranquilizers; muscle relaxants; antihistamines; hypotensive agents; cardioactive agents; angiotensin converting enzyme inhibitors; bronchodilators; steroids; antibacterial agents; antimalarials; antibiotics, sedatives and analgesics.

25. The sustained release tablet of claim 24, wherein said active coating contains said active agent in an amount of from about 15 to 33% by weight of the total dosage weight of said active agent in the tablet.

26. The sustained release tablet of claim 12, wherein said plasticizer in said barrier coating, said active coating and said film coating comprises glyceryl triacetate.

27. The sustained release tablet of claim 12, wherein said active agent comprises 30% to 80% by weight of said core; said soluble polymer to said insoluble polymer in said barrier coating is at a weight ratio of from about 1:1 to 1:10, and said plasticizer comprises about 5% to 20% by weight of said barrier coating.

28. The sustained release tablet of claim 27, wherein said insoluble polymer in said tablet core and said barrier coating comprises ethyl cellulose.

29. The sustained release tablet of claim 27, wherein said soluble polymer in said barrier coating is selected from the group consisting of hydroxypropyl methylcellulose, hydroxypropyl cellulose, methylcellulose, carboxymethyl cellulose, and mixtures thereof.

30. The sustained release tablet of claim 27, wherein said soluble polymer in said barrier coating, said active coating, and said film coating comprises hydroxypropyl methyl cellulose.

31. The sustained release tablet of claim 27, wherein said active coating contains said active agent in an amount of from about 1 to about 35% by weight of the total dosage weight of said active agent in the tablet.

32. The sustained release tablet of claim 31, wherein said active coating contains said active agent in an amount of from about 15 to about 33% by weight of the total dosage weight of said active agent in the tablet.

33. The sustained release tablet of claim 31, wherein said active agent in said tablet core and said active coating comprises phenylpropanolamine hydrochloride.

34. The sustained release tablet of claim 27, wherein said active agent is selected from the group consisting of adrenergic agents; cholinergic agents; antispasmodic agents; curariform agents; tranquilizers; muscle relaxants; antihistamines; hypotensive agents; cardioactive agents; angiotensin converting enzyme inhibitors; bronchodilators; steroids; antibacterial agents; antimalarials; antibiotics, sedatives and analgesics.

35. The sustained release tablet of claim 27, wherein said plasticizer in said barrier coating, said active coating and said film coating comprises glyceryl triacetate.

36. A sustained release tablet adapted to provide an initial immediate release of phenylpropanolamine hydrochloride, a period of no release of phenylpropanolamine hydrochloride followed by a substantially constant, rate of release of phenylpropanolamine hydrochloride, the tablet comprising:

(a) a compressed tablet core comprising phenylpropanolamine hydrochloride, ethyl cellulose and calcium sulfate;

(b) a barrier coating formed over said compressed tablet core, said barrier coating comprising a mixture of hydroxypropyl methyl cellulose, ethyl cellulose and glyceryl triacetate, wherein said hydroxypropyl methyl cellulose and said ethyl cellulose are utilized in a ratio by weight of about 1:3;

(c) an active coating formed over said barrier coating, said active coating comprising phenylpropanolamine hydrochloride, hydroxypropyl methyl cellulose and glyceryl triacetate, wherein the amount of phenylpropanolamine hydrochloride in said active coating is from about 15 to about 33% by weight of the total dosage weight of said phenylpropanolamine hydrochloride in said sustained release tablet; and (d) a film coating formed over said active coating, said film coating comprising hydroxypropyl methyl cellulose and glyceryl triacetate.

* * * * *

UNITED STATES PATENT AND TRADEMARK OFFICE
CERTIFICATE OF CORRECTION

PATENT NO. : 5,407,686
DATED : April 18, 1995
INVENTOR(S) : S. PATEL et al.

It is certified that error appears in the above-indentified patent and that said Letters Patent is hereby corrected as shown below:

On title page, item [75], Inventors, line 1, change "Satischandra" to ---Satishchandra---.

Signed and Sealed this

Seventeenth Day of October, 1995

Attest:

BRUCE LEHMAN

Attesting Officer  Commissioner of Patents and Trademarks